US00PP35840P2

(12) United States Plant Patent
Rupp

(10) Patent No.: US PP35,840 P2
(45) Date of Patent: May 28, 2024

(54) ***DIANTHUS* PLANT NAMED 'KLEDG22394'**

(50) Latin Name: ***Dianthus caryophyllus* L.**
Varietal Denomination: KLEDG22394

(71) Applicant: KLEMM + SOHN GMBH & CO. KG, Stuttgart (DE)

(72) Inventor: Judith Rupp, Stuttgart (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 18/209,612

(22) Filed: Jun. 14, 2023

(51) Int. Cl.
*A01H 5/02* (2018.01)
*A01H 6/30* (2018.01)

(52) U.S. Cl.
USPC ..... Plt./273
CPC ..... *A01H 6/305* (2018.05)

(58) Field of Classification Search
USPC ..... Plt./273
CPC ..... A01H 6/305; A01H 5/02
See application file for complete search history.

*Primary Examiner* — Keith O. Robinson
(74) *Attorney, Agent, or Firm* — Weatherly IP Solutions, LLC; James M. Weatherly

(57) ABSTRACT

A new *Dianthus* plant designated 'KLEDG22394' particularly distinguished by single, white flowers with purple patterns with winter hardiness, is disclosed.

1 Drawing Sheet

Genus and species: *Dianthus caryophyllus* L.
Variety denomination: 'KLEDG22394'.

BACKGROUND OF THE NEW PLANT

The present invention comprises a new and distinct variety of *Dianthus*, botanically known as *Dianthus caryophyllus* L., and hereinafter referred to by the variety name 'KLEDG22394'. 'KLEDG22394' originated from a cross pollination from the proprietary female parent 'DSS-2014-1025' (unpatented) and proprietary male parent 'DSS-2014-1002' (unpatented) in 2015 between May and August in Stuttgart, Germany.

A plant line was selected in June 2016 in Stuttgart, Germany, and named 'KLEDG22394'. In July 2016, 'KLEDG22394' was first vegetatively propagated by vegetative stem cuttings in Stuttgart, Germany. 'KLEDG22394' was found to reproduce true to type in successive generations of asexual propagation in Stuttgart, Germany via vegetative cuttings.

SUMMARY

The following are the most outstanding and distinguishing characteristics of 'KLEDG22394' when grown under normal horticultural practices in Stuttgart, Germany.

1. Single, white flowers with purple patterns; and
2. Winter-hardiness.

DESCRIPTION OF THE PHOTOGRAPH

This new *Dianthus* plant is illustrated by the accompanying photograph of a 14-week-old plant taken in March 2019 and grown indoors in Stuttgart, Germany. The colors shown are as true as can be reasonably obtained by conventional photographic procedures. The photograph is a whole plant photo of 'KLEDG22394' and shows the foliage, buds, and flowers.

DESCRIPTION

The following detailed descriptions set forth the distinctive characteristics of 'KLEDG22394'. The data which define these characteristics were collected from asexual reproductions carried out in Latina, Italy. Data was collected in March 2023 from 21-week-old plants that were potted in October 2022 and grown in a plastic greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus caryophyllus* L.
- *Designation*.—'KLEDG22394'.
- *Type*.—Pot carnation.

Parentage
- *Female patent*.—'DSS-2014-1025' (unpatented).
- *Male parent*.—'DSS-2014-1002' (unpatented).

Plant:
- *Propagation type*.—Vegetative cuttings.
- *Time to produce a rooted young plant*.—28 days.
- *Root description*.—Fine; roots, color is white, RHS 155A.
- *Rooting habit shape*.—Lanceolate.
- *Plant form*.—Upright.
- *Plant height*.—15.0 cm.
- *Plant diameter or spread*.—22.0 cm.

Lateral branches/stems:
- *Shape of the branch in cross-section*.—Circular.
- *Hollowness of the branch*.—Absent.
- *Length*.—15.0 cm.
- *Diameter*.—0.2 cm.
- *Thickness*.—Medium.
- *Internode length*.—3.2 cm.
- *Internode quantity per branch*.—4.
- *Number of internodes per branch/stem*.—4.
- *Node length*.—0.2 cm.
- *Node diameter*.—0.6 cm.
- *Texture*.—Smooth.
- *Color*.—RHS 138A.
- *Flower clustering on the lateral branch*.—In some lateral branches.

Foliage:
*Arrangement*.—Opposite.
*Length*.—7.5 cm.
*Width*.—0.6 cm.
*Shape*.—Obovate.
*Apex*.—Acute.
*Base*.—Obtuse.
*Margin*.—Entire.
*Texture* (*both upper and lower surfaces*).—Smooth.
*Cross-section of the leaf*.—Strongly concave.
*Curvature of the leaf*.—Absent.
*Glaucosity of the leaf*.—Weak.
*Leaf color* (*both immature and mature*).—Immature: Upper surface: RHS 138B. Lower surface: RHS 138A. Mature: Upper surface: RHS N138A. Lower surface: RHS N138B.
*Venation pattern*.—Absent.

Flowers:
*Flower type*.—Semi-double.
*Fragrance*.—Semi-sweet.
*Position of the flowers compared to the foliage of the plant*.—Same level.
*Profile of both the upper and lower part in the lateral view*.—Flat convex.
*Diameter of the flower*.—3.6 cm.
*Natural flowering season*.—Spring to Autumn.
*Number of flowers per spray*.—1-3.
*Flower longevity on the plant*.—14 days.

Buds:
*Length*.—2.0 cm.
*Diameter*.—0.6 cm.
*Shape*.—Oblong.
*Color*.—RHS 137A.
*Extrusion of the styles at the bud stage*.—Absent.

Corolla:
*Quantity of petals and arrangement*.—6 and arranged in several whorls.
*Corolla height*.—1.0 cm.
*Petal length*.—3.6 cm.
*Petal width*.—2.1 cm.
*Petal shape*.—Obtuse.
*Petal apex*.—Obtuse.
*Petal base*.—Acute.
*Petal margin*.—Crenate.
*Depth of petal margin*.—Shallow.
*Petal texture* (*both upper and lower surfaces*).—Smooth.
*Petal color*.—Immature: Upper surface: RHS NN155C with RHS 187B. Lower surface: RHS 157A. Mature: Upper surface: RHS NN155C and RHS 187C. Lower surface: RHS NN155B.
*Macule*.—Present RHS NN155B. Size: 0.4 cm to 0.6 cm.
*Calyx*.—Quantity of sepals: Composed of 5 sepals. Longitudinal axis of the lobes of the calyx: Straight. Shape: Cylindrical. Calyx height: 2.0 cm. Calyx diameter (at the apex): 0.8 cm. Sepal texture (both upper and lower surfaces): Smooth. Sepal color: Upper surface: RHS N137B. Lower surface: RHS 138B.
*Position of the outer lobes of the epicalyx in relation to the calyx*.—Adpressed.
*Apex shape of the outer lobes of the epicalyx*.—Short acuminate.
*Apex shape of the inner lobes of the epicalyx*.—Short acuminate to medium acuminate.
*Tip length of the inner lobes of the epicalyx*.—0.1 cm.

Peduncles:
*Length*.—2.5 cm.
*Diameter*.—0.2 cm.
*Strength*.—Medium.
*Texture*.—Smooth.
*Color*.—RHS 136A.

Reproductive organs:
*Stamens*.—Quantity per flower: 6. Filament length: 1.3 cm. Filament color: RHS NN155A. Anther length: 0.2 cm. Anther diameter: Less than 0.01 cm. Anther color: RHS 160C. Pollen amount: None observed.
*Pistils*.—Quantity per flower: 2. Length: 1.9 cm. Diameter: 0.1 cm. Stigma: Color: RHS 68B. Shape: Filamentous. Length: 0.3 cm. Diameter: 0.1 cm. Style: Number: Two. Shoulder: Absent. Color: RHS N155B. Length: 1.6 cm. Diameter: 0.1 cm. Ovary: Color: RHS145C. Width: 0.6 cm. Shape: Obovate. Texture: Smooth.

Fruit and seed set: None observed.

Disease and pest/insect resistance: No particular disease or insect resistance observed.

COMPARISON WITH PARENTAL LINE AND KNOWN VARIETY

'KLEDG22394' is distinguished from the parental line as described in Table 1.

TABLE 1

Comparison with Parental Line

| Characteristic | 'KLEDG22394' | Female Parent 'DSS-2014-1025' | Male Parent 'DSS-2014-1002' |
|---|---|---|---|
| Flower color | White and purple pattern | Purple | Light pink and purple pattern |

'KLEDG22394' can be compared to the unpatented *Dianthus* variety 'KLEDP07089' (unpatented). Differences between the varieties are described in Table 2.

TABLE 2

Comparison with Similar Variety

| Characteristic | 'KLEDG22394' | 'KLEDP07089' |
|---|---|---|
| Flower color | White and purple pattern | Pink and purple pattern |
| Winter-hardy | Yes | No |
| Flower | Semi-double | Semi-double |

I claim:

1. A new and distinct cultivar of *Dianthus* Plant Named 'KLEDG22394' as described and illustrated herein.

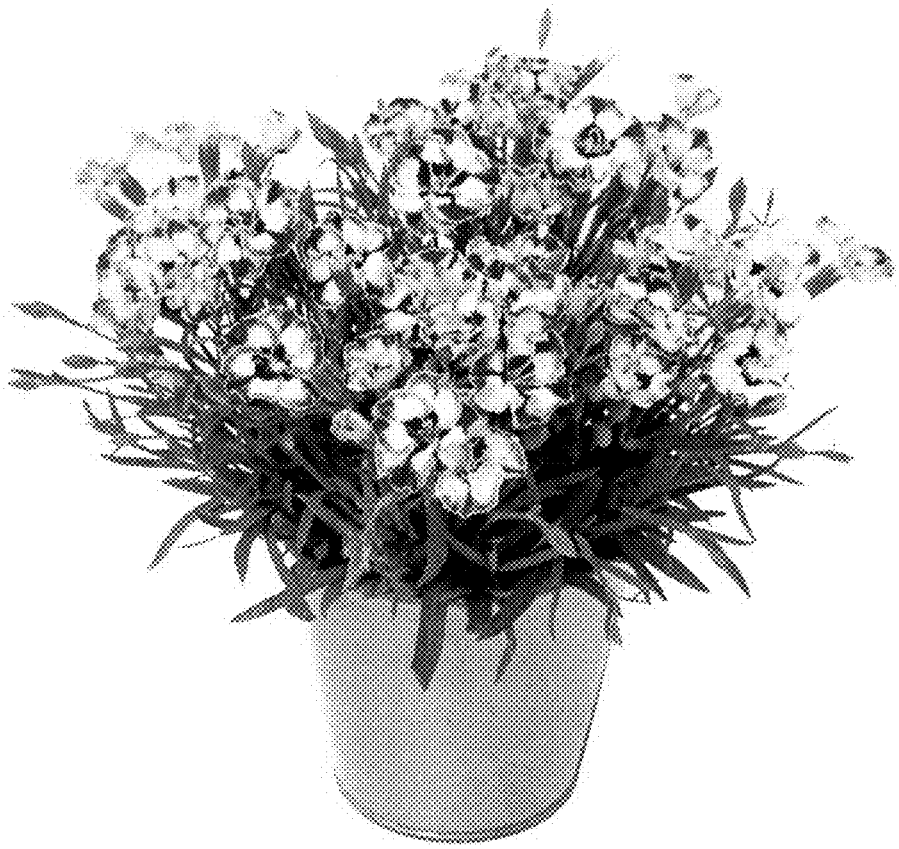

* * * * *